(12) United States Patent
Kato et al.

(10) Patent No.: US 10,317,328 B2
(45) Date of Patent: Jun. 11, 2019

(54) INTERNAL COMBUSTION ENGINE

(71) Applicant: TOYOTA JIDOSHA KABUSHIKI KAISHA, Toyota-shi, Aichi-ken (JP)

(72) Inventors: Akira Kato, Sunto-gun (JP); Go Hayashita, Chigasaki (JP)

(73) Assignee: Toyota Jidosha Kabushiki Kaisha, Toyota-shi, Aichi-ken (JP)

(*) Notice: Subject to any disclaimer, the term of this patent is extended or adjusted under 35 U.S.C. 154(b) by 112 days.

(21) Appl. No.: 15/324,026

(22) PCT Filed: Jul. 24, 2015

(86) PCT No.: PCT/JP2015/003723
§ 371 (c)(1),
(2) Date: Jan. 5, 2017

(87) PCT Pub. No.: WO2016/031132
PCT Pub. Date: Mar. 3, 2016

(65) Prior Publication Data
US 2017/0205326 A1     Jul. 20, 2017

(30) Foreign Application Priority Data
Aug. 26, 2014 (JP) ................................. 2014-171893

(51) Int. Cl.
*G01N 15/06* (2006.01)
*G01N 27/406* (2006.01)
(Continued)

(52) U.S. Cl.
CPC ..... *G01N 15/0656* (2013.01); *G01N 15/0606* (2013.01); *G01N 27/409* (2013.01); *G01N 27/4067* (2013.01); *G01N 27/41* (2013.01)

(58) Field of Classification Search
CPC .... G01N 15/10; G01N 15/102; G01N 15/104; G01N 27/404–27/407; G01N 27/409;
(Continued)

(56) References Cited

U.S. PATENT DOCUMENTS

| 2004/0000493 A1 | 1/2004 | Yasui et al. |
| 2011/0265551 A1 | 11/2011 | Hopka et al. |

(Continued)

FOREIGN PATENT DOCUMENTS

| JP | H11-229859 A | 8/1999 |
| JP | 2003-329633 A | 11/2003 |

(Continued)

OTHER PUBLICATIONS

M. Li et al., "A Family of Oxide Ion Conductors Based on the Ferroelectric Perovskite $Na_{0.5}Bi_{0.5}TiO_3$", Nature Materials, vol. 13, pp. 31-35, Jan. 2014.

(Continued)

*Primary Examiner* — Gurpreet Kaur
(74) *Attorney, Agent, or Firm* — Finnegan, Henderson, Farabow, Garrett & Dunner, LLP

(57) ABSTRACT

An internal combustion engine includes an ECU, an A/F sensor being active at a first temperature lower than a PM combustion temperature and set in advance, and a heater to heat the A/F sensor to a second temperature equal to or higher than the PM combustion temperature and set in advance. The ECU detects PM based on a difference between an output value of the A/F sensor at the first temperature and an output value of the A/F sensor at the second temperature. The ECU may perform determining that a PM accumulation amount is smaller than a reference amount when the output value is higher than a threshold value, and that the PM accumulation amount is equal to or
(Continued)

larger than the reference amount when the output value is a value equal to or smaller than the threshold value.

7 Claims, 11 Drawing Sheets

(51) Int. Cl.
*G01N 27/409* (2006.01)
*G01N 27/41* (2006.01)

(58) Field of Classification Search
CPC .................. G01N 27/419; G01N 27/41; F01N 2560/00–2560/20; F01N 2550/00–2550/24; F02D 41/123; F02D 41/1454
See application file for complete search history.

(56) References Cited

U.S. PATENT DOCUMENTS

| | | | |
|---|---|---|---|
| 2012/0031168 A1* | 2/2012 | Sakamoto | F01N 11/00 73/23.33 |
| 2015/0275738 A1* | 10/2015 | Van Nieuwstadt | B01D 46/0086 73/114.76 |

FOREIGN PATENT DOCUMENTS

| | | |
|---|---|---|
| JP | 2005-337782 | 12/2005 |
| JP | 2009-281974 | 12/2009 |
| JP | 2009-293466 | 12/2009 |
| JP | 2010-261782 | 11/2010 |
| JP | 2011-80439 | 4/2011 |
| JP | 2012-037370 A | 2/2012 |
| JP | 2012-219673 A | 11/2012 |
| JP | 2013-174448 A | 9/2013 |

OTHER PUBLICATIONS

K. Fukuda et al., "Crystal Structure and Oxide-Ion Conductivity along c-Axis of Si-Deficient Apatite-Type Lanthanum Silicate", Chemistry of Materials, vol. 25, pp. 2154-2162, 2013.

H. Yoshioka et al., "Ionic Conductivity and Fuel Cell Properties of Apatite-type Lanthanum Silicates Doped with Mg and Containing Excess Oxide Ions", Solid State Ionics, vol. 179, pp. 2165-2169, 2008.

* cited by examiner

[Fig. 1]
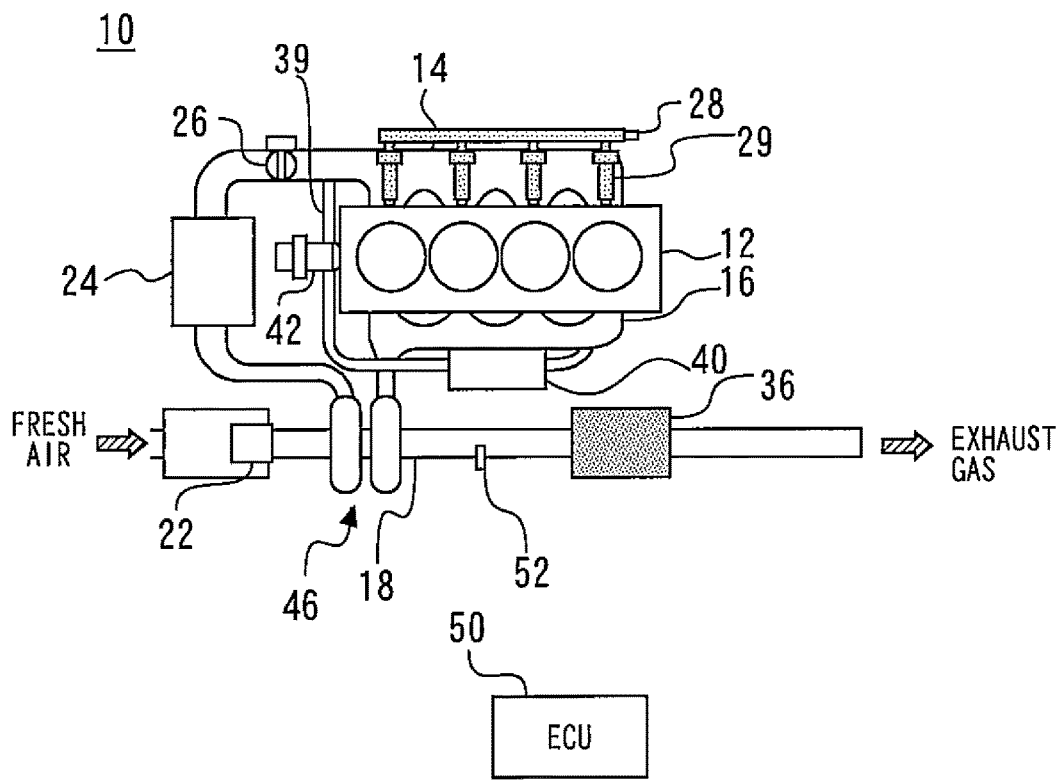
[Fig. 2]
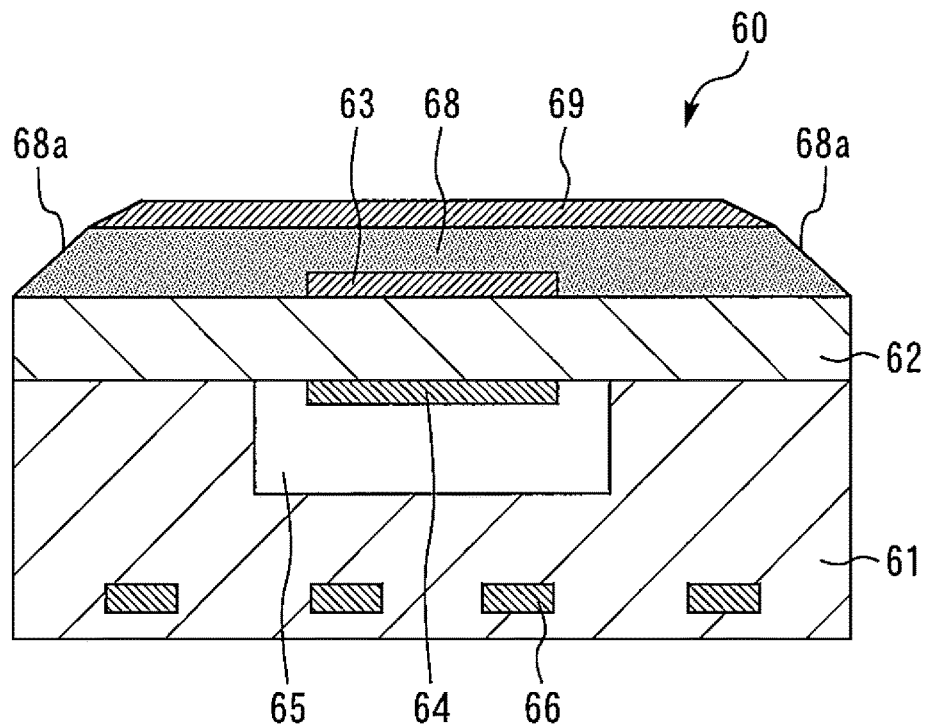

[Fig. 3]
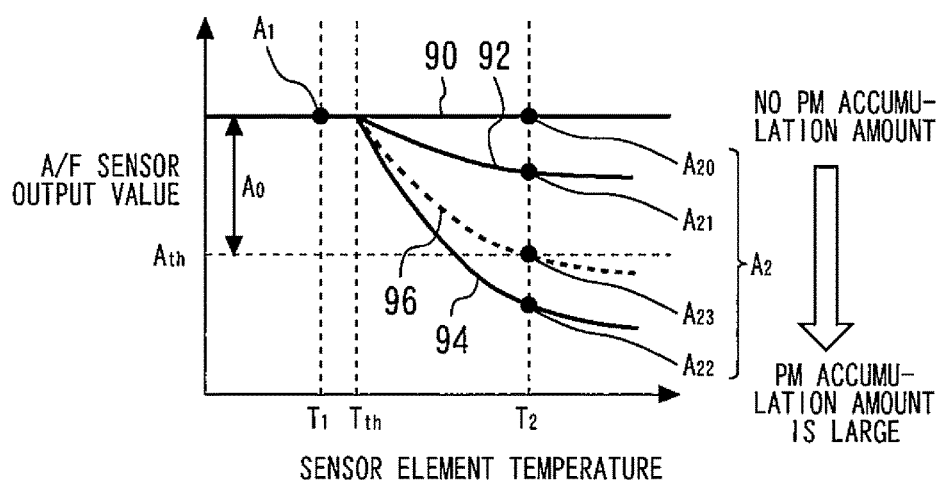

[Fig. 4]
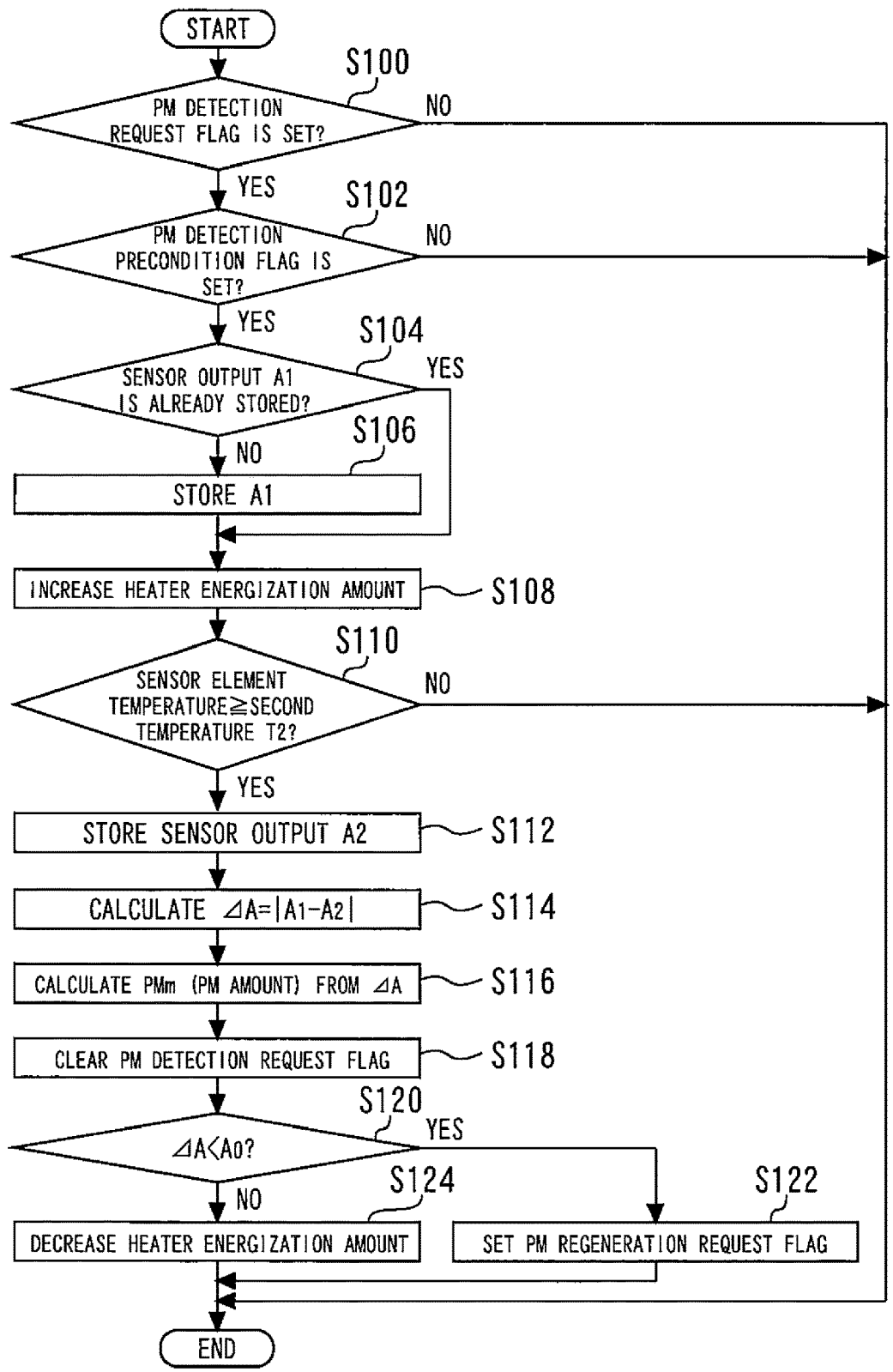

[Fig. 5]
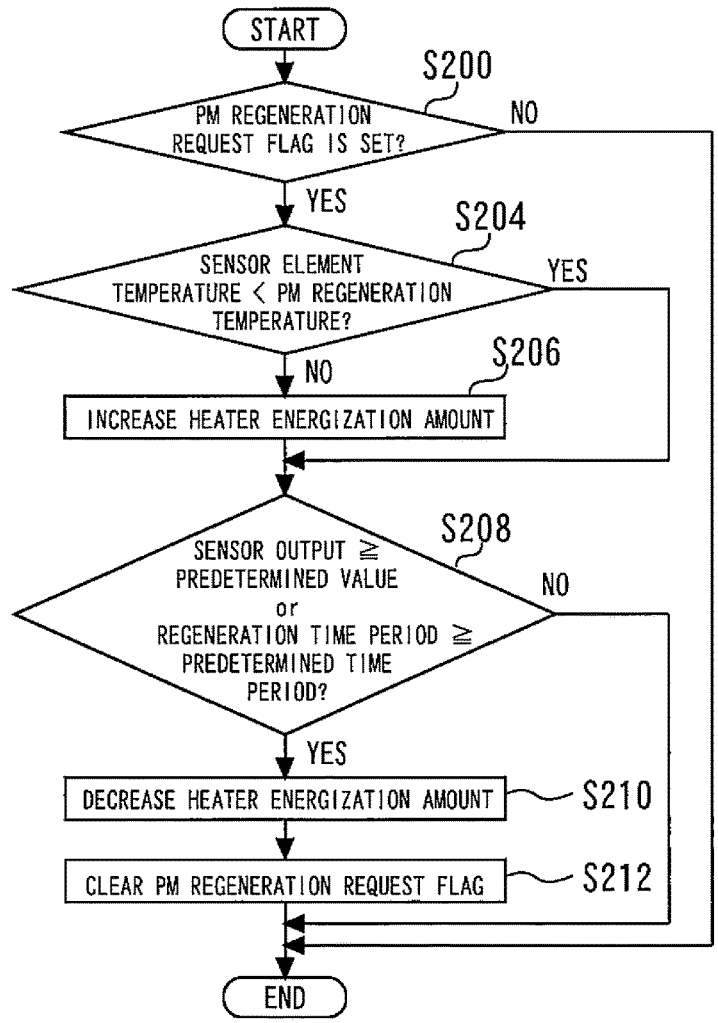
[Fig. 6]
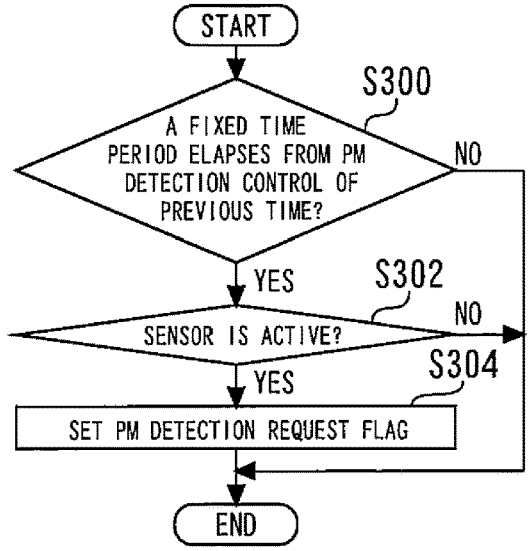

[Fig. 7]
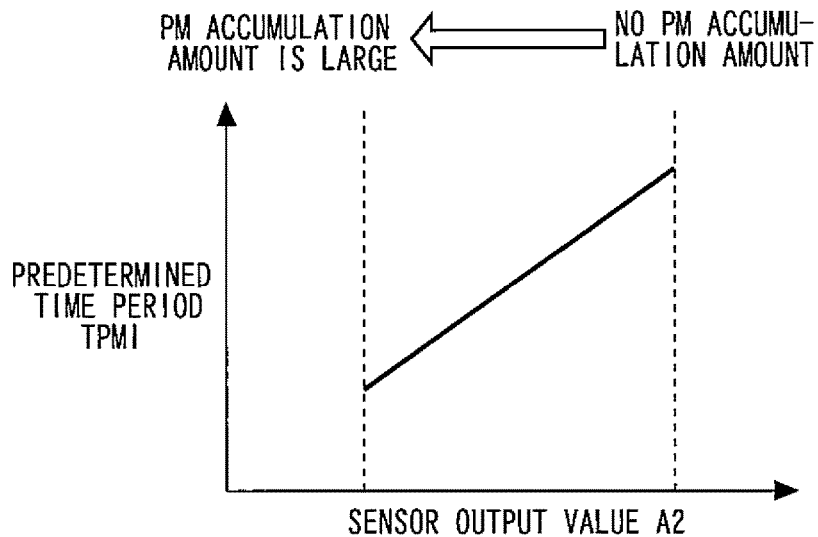
[Fig. 8]
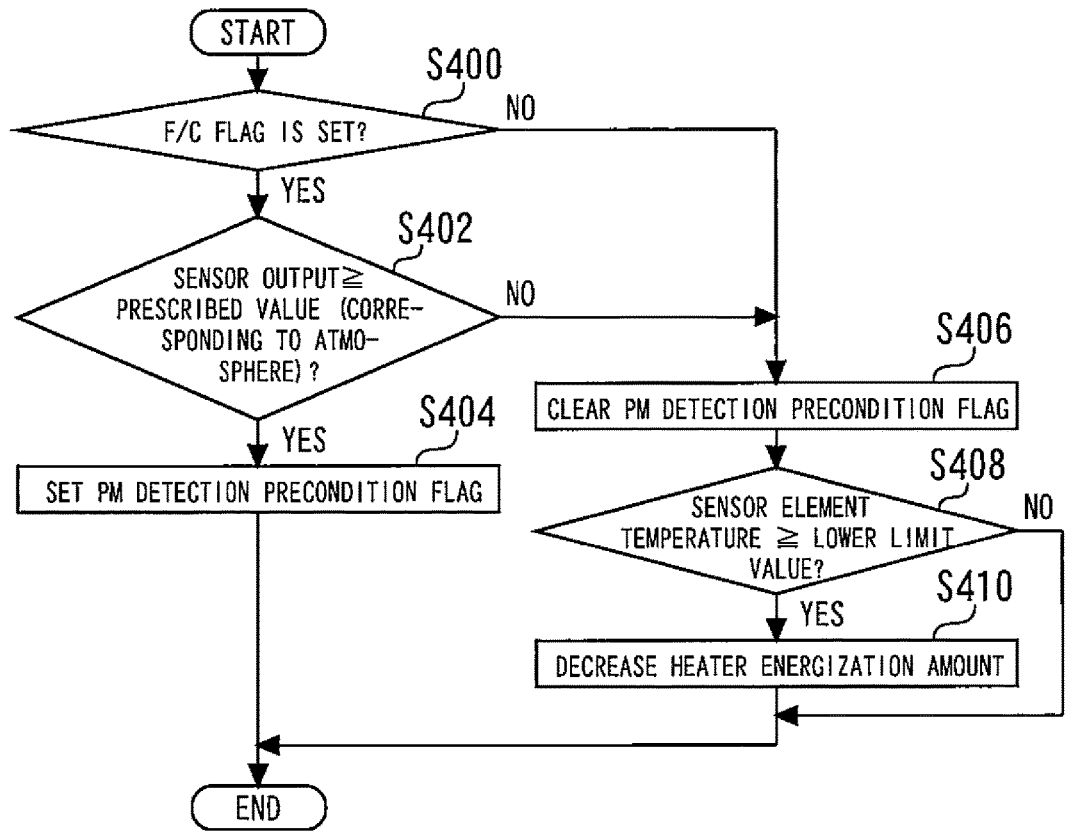

[Fig. 9]
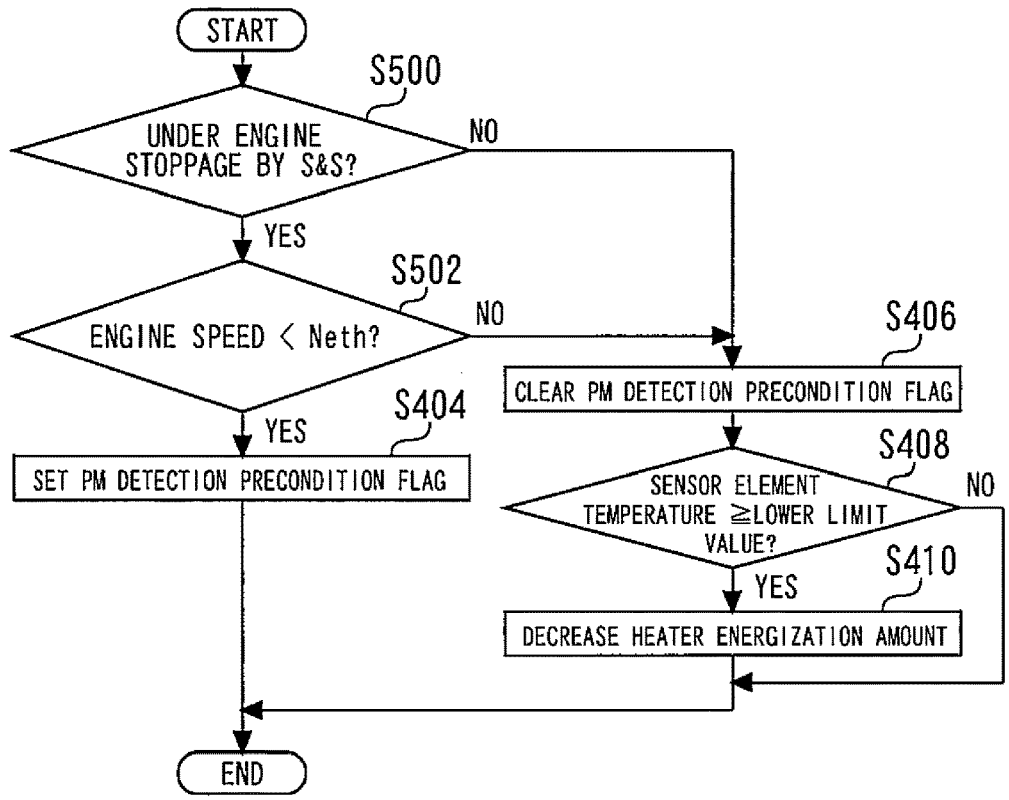
[Fig. 10]
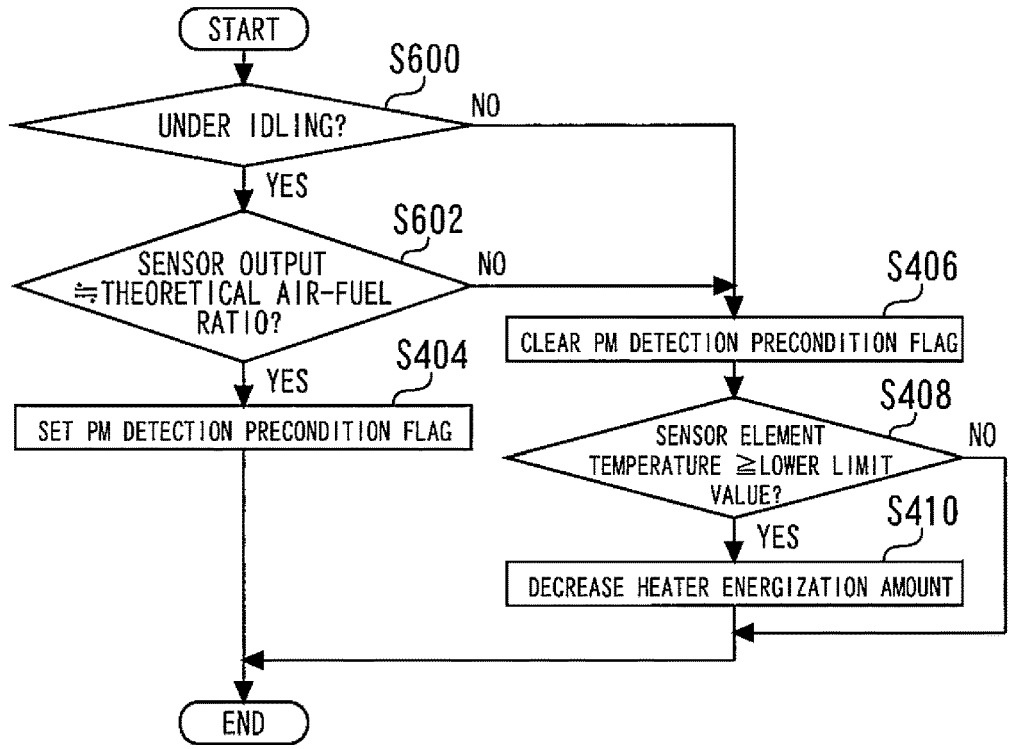

[Fig. 11]
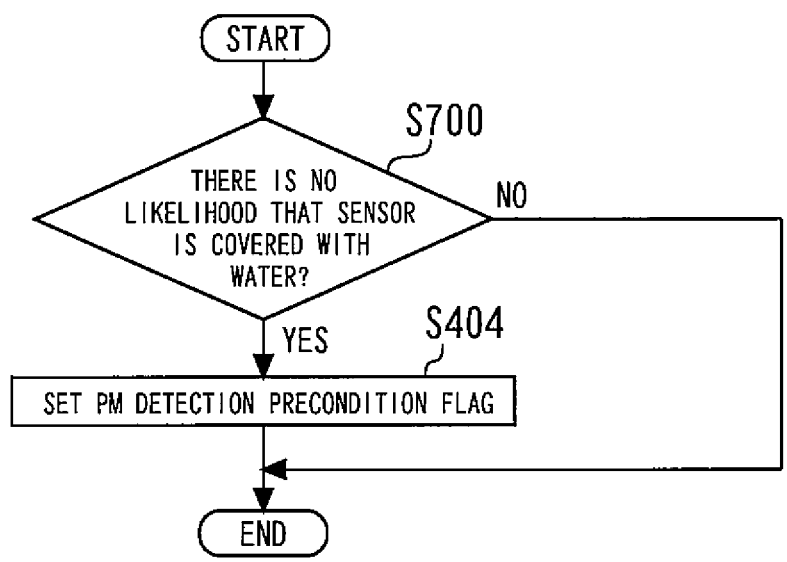

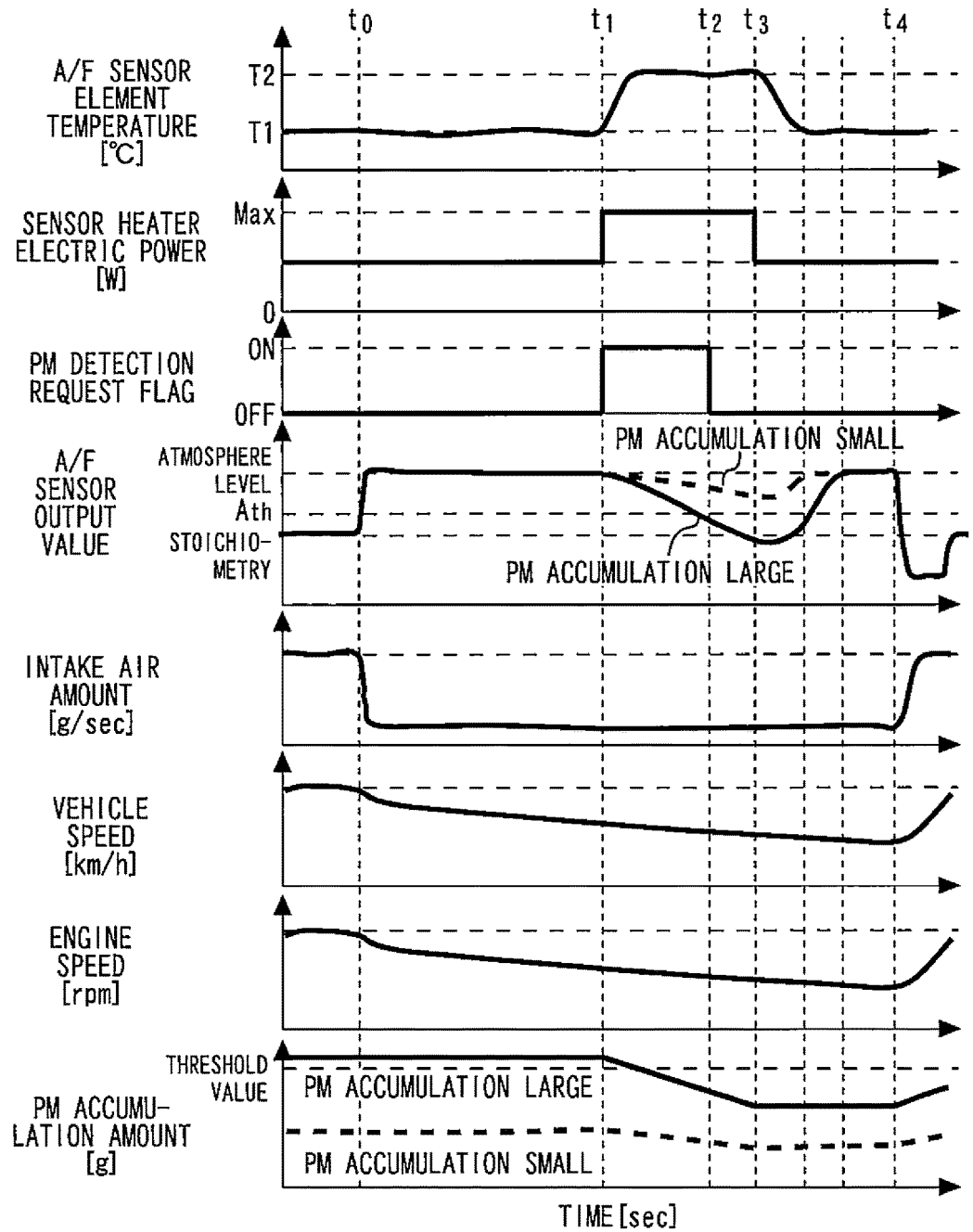
[Fig. 12]

[Fig. 13]
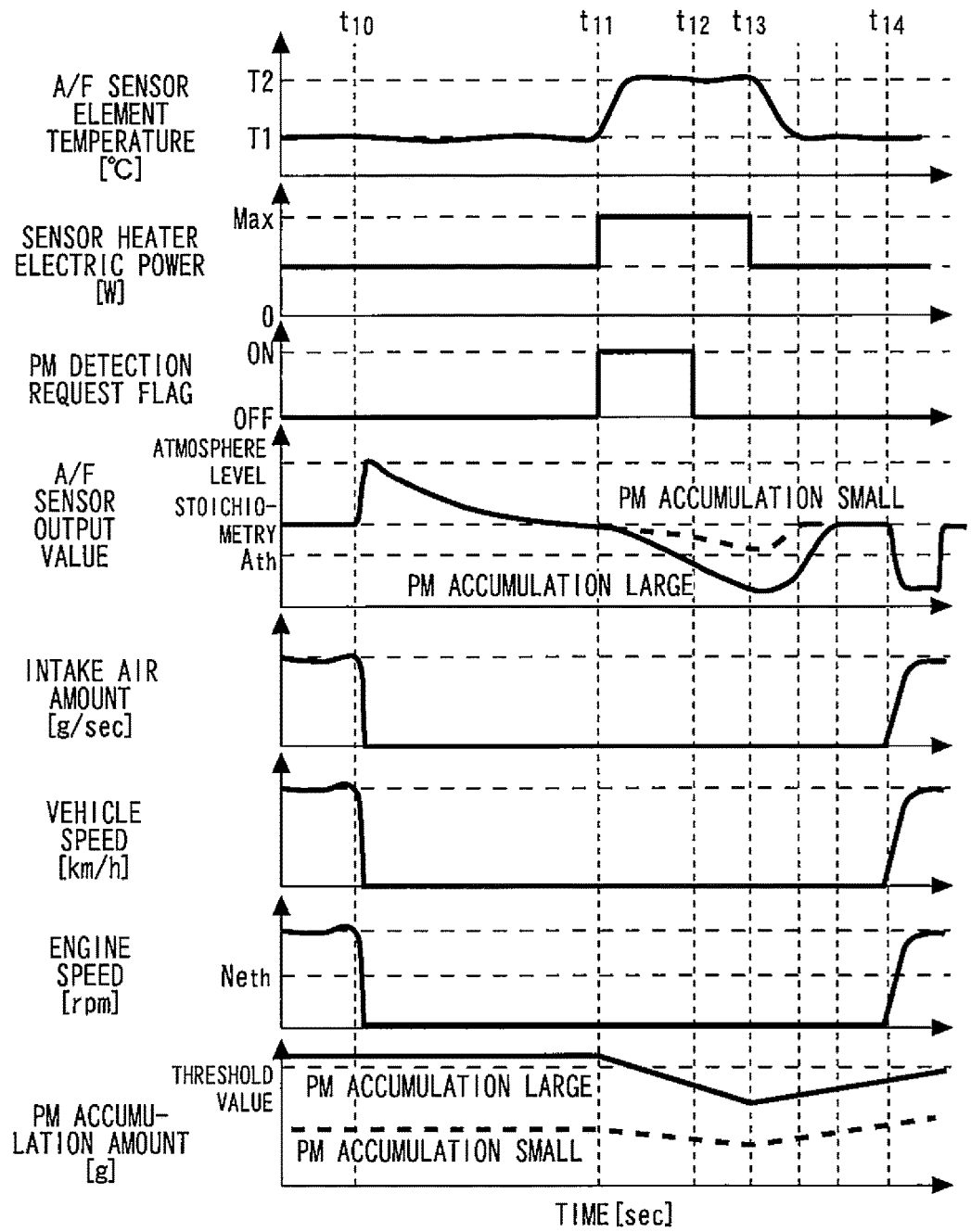

[Fig. 14]
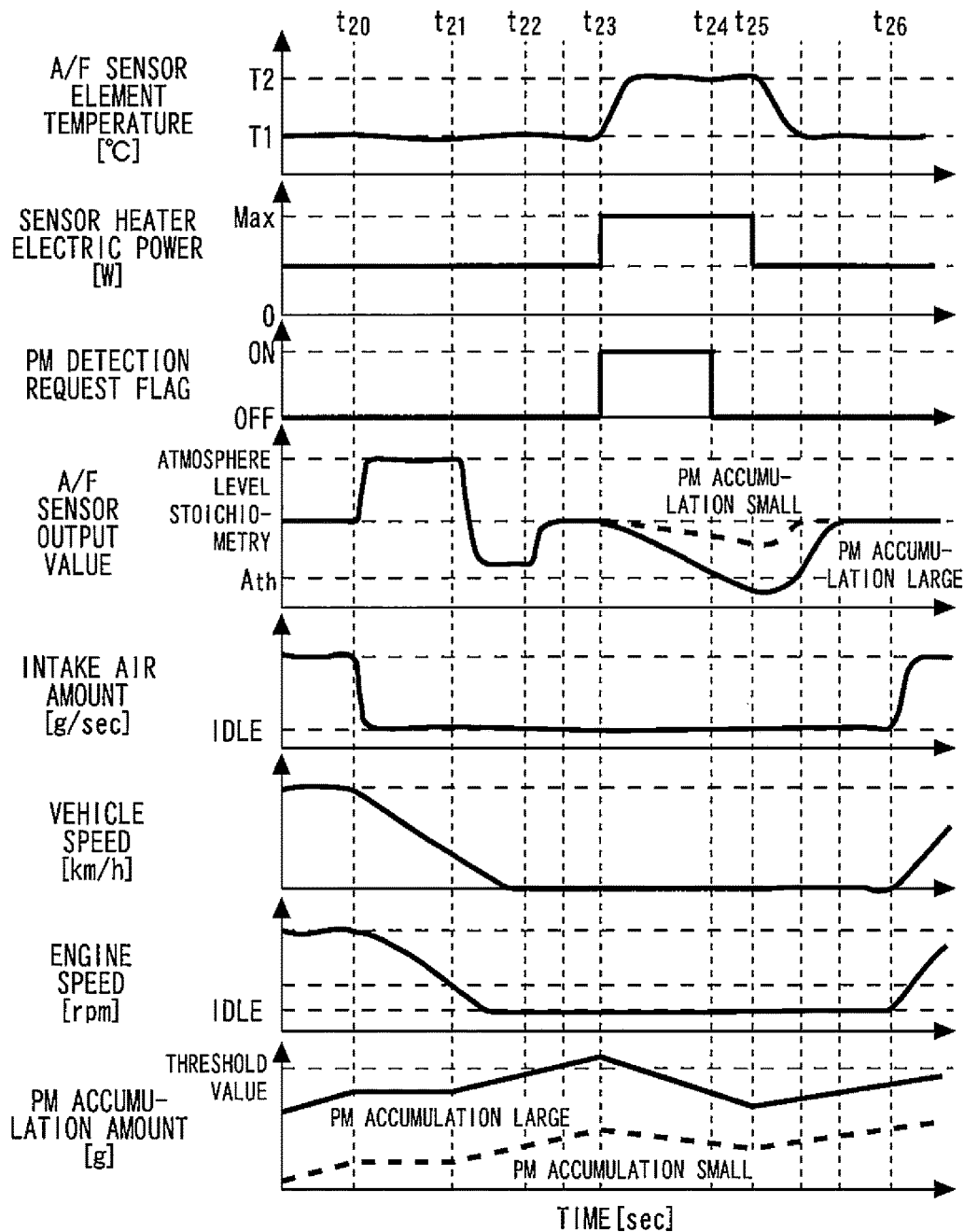

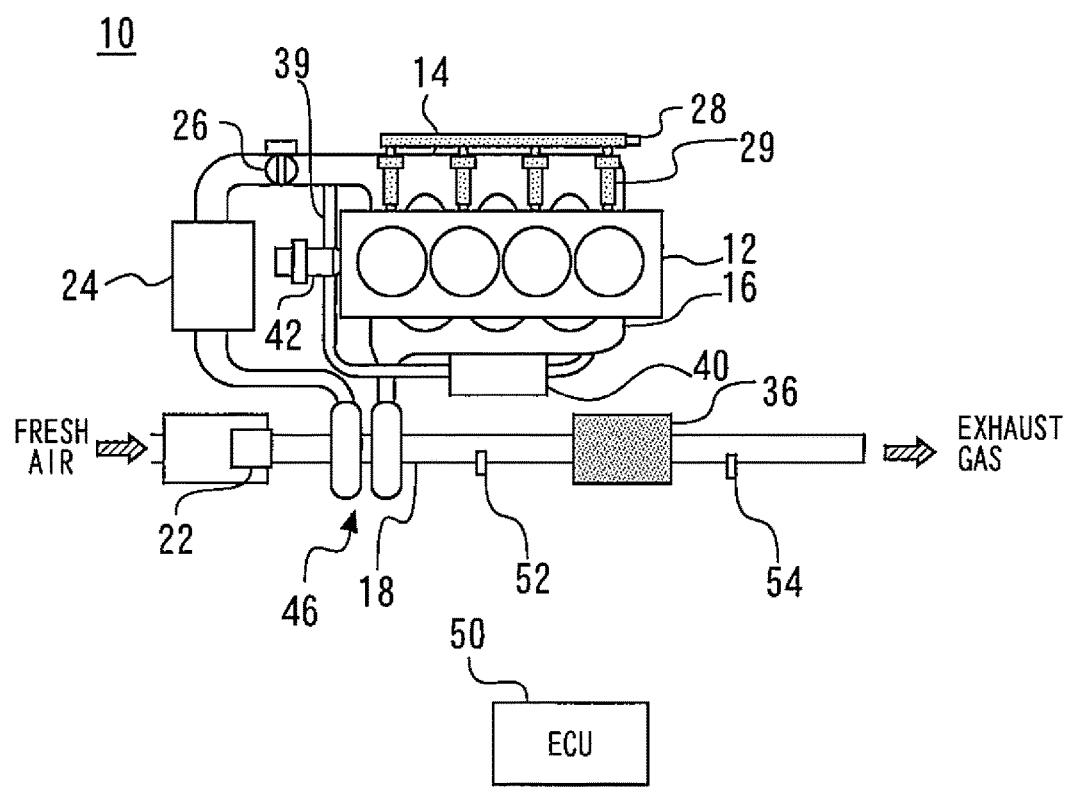
[Fig. 15]

INTERNAL COMBUSTION ENGINE

CROSS-REFERENCE TO RELATED APPLICATIONS

This application is a national phase application of International Application No. PCT/JP2015/003723, filed Jul. 24, 2015, and claims the priority of Japanese Application No. 2014-171893, filed Aug. 26, 2014, the content of both of which is incorporated herein by reference.

TECHNICAL FIELD

The present invention relates to an internal combustion engine.

BACKGROUND ART

Conventionally, there has been known a soot detecting device that detects particulate matter that is generated in an internal combustion engine or the like, more specifically, soot composed of carbon, as is disclosed in Japanese Patent Laid-Open No. 2009-281974, for example. The particulate matter is also abbreviated as "PM" in general. The soot detecting device according to the publication includes an oxygen ion conductor such as stabilized zirconia, heating means that heats an oxygen ion conductor, a first oxygen concentration measuring section that measures an oxygen concentration which is changed by combustion of soot. The temperature of the oxygen ion conductor is controlled to the temperature at which soot remains and combustion of the soot is enabled by oxygen (active oxygen) that is supplied by pumping. At a time of detection of soot, a voltage is applied to between both electrodes at the oxygen ion conductor to perform pumping of oxygen, and by using the pumped oxygen, soot is combusted at the controlled temperature. Since the first oxygen concentration measuring section issues an output (a current value, for example) indicating an oxygen concentration, detection of soot (calculation of the amount of soot or the like) can be performed by using the output. However, the above described conventional art performs oxygen pumping by applying a voltage to between both the electrodes at the oxygen ion conductor while keeping the control temperature in a fixed range, and does not change the control temperature intentionally.

CITATION LIST

Patent Literature

PTL 1: Japanese Patent Laid-Open No. 2009-281974

Non Patent Literature

NPL 1: Ming Li et al., "A family of oxide ion conductors based on the ferroelectric perovskite Na0.5Bi0.5TiO3", NATURE MATERIALS. VOL 13. JANUARY 2014
NPL 2: Koichiro Fukuda et al., "Crystal Structure and Oxide-Ion Conductivity along c-Axis of Si-Deficient Apatite-Type Lanthanum Silicate", CHEMISTRY OF MATERIALS, 2013, 25, 2154-2162
NPL 3: Hideki Yoshioka et al., "Ionic conductivity and fuel cell properties of apatite-type lanthanum silicates doped with Mg and containing excess oxide ions", Solid State Ionics 179 (2008) 2165-2169

According to the research results of recent years, solid electrolyte materials that indicate high oxygen ion conductivities at a relatively low temperature have been found out as shown in the above described Non Patent Literatures 1 to 3 as examples. The oxygen concentration sensors using the solid electrolyte materials illustrated in Non Patent Literatures 1 to 3 can exhibit performance that is equivalent to the performance at the time of the activation temperature of the conventional oxygen concentration sensor, at a lower temperature. That is to say, the solid electrolyte materials as above are used in the oxygen concentration sensors, whereby the activation temperatures of the oxygen concentration sensors can be lowered more than the conventional material such as zirconia, and the oxygen concentration sensors can be activated at a temperature lower than the PM combustion temperature. Therefore, the inventor of the present application has found out a novel art that can detect PM with high precision by using the oxygen concentration sensor which is in an active state at a low temperature like this.

SUMMARY

An object of the present invention is to provide an internal combustion engine that can perform PM detection with favorable precision by using an oxygen concentration sensor.

An internal combustion engine according to one aspect of the present invention, includes: an oxygen concentration sensor; and a control device that executes PM detection control that detects PM based on an output value of the oxygen concentration sensor. The oxygen concentration sensor is provided in an exhaust passage. The oxygen concentration sensor is in an active state at a first temperature which is lower than a PM combustion temperature and is set in advance, and a second temperature which is equal to or higher than the PM combustion temperature and is set in advance. The PM detection control is configured to (i) acquire one output value of a first output value of the oxygen concentration sensor at a time of the oxygen concentration sensor being at the first temperature, and a second output value of the oxygen concentration sensor at a time of the oxygen concentration sensor being at the second temperature, (ii) acquire the other output value of the first output value and the second output value after acquiring the one output value, (iii) detect PM based on a difference between or a ratio of the first output value and the second output value. The second output value is acquired at a same time as the oxygen concentration sensor reaches the second temperature, or at a time when a predetermined time period which is set in advance elapses after a temperature rise of the oxygen concentration sensor to the second temperature occurs.

A heater to heat the oxygen concentration sensor to the second temperature may be provided in the above aspect of the present invention. The PM detection control may be configured to heat the oxygen concentration sensor to the second temperature with the heater after acquiring the first output value, and after heating to the second temperature by the heater, the PM detection control may acquire an output value of the oxygen concentration sensor at a time when the predetermined time period elapses, as the second output value.

The control device may be configured to execute PM regeneration control. The PM regeneration control may be configured to control the heater to keep the oxygen concentration sensor at the PM combustion temperature or a higher temperature than the PM combustion temperature when a difference between or a ratio of an output value of the oxygen concentration sensor at the first temperature and an output value of the oxygen concentration sensor at the second temperature is larger than a value set in advance, after heating the oxygen concentration sensor to the second temperature with the heater.

The control device may be configured not to perform the PM detection control of a next time until a predetermined time period which is set in advance elapses, after executing the PM detection control. The control device may be configured to execute time setting control that sets the predetermined time period to be longer as a reduction amount of the second output value relative to the first output value in the PM detection control of a previous time is smaller.

The control device may be configured to execute the PM detection control in at least one of time periods during fuel cut, during an idle operation and during idle stop.

The control device may be configured not to execute the PM detection control when an operation condition of the internal combustion engine corresponds to a condition set in advance under which the oxygen concentration sensor is likely to be covered with water.

The PM detection control may be configured to calculate a larger amount of PM, as a detected reduction amount is larger. The detected reduction amount is a reduction amount of an output value of the oxygen concentration sensor at a time of the second temperature relative to the output value of the oxygen concentration sensor at a time of the first temperature.

According to the above aspect of the present invention, the oxygen concentration sensor is active at both the first and the second temperatures, and a plurality of sensor output values for use in PM detection all have correlations with an oxygen concentration with high precision. Accordingly, the oxygen concentration change following PM combustion can be measured with high precision, and PM detection can be performed with favorable precision.

BRIEF DESCRIPTION OF DRAWINGS

FIG. 1 is a schematic diagram showing an internal combustion engine according to an embodiment of the present invention.

FIG. 2 is a view showing the A/F sensor included by the engine according to the embodiment of the present invention.

FIG. 3 is a diagram for explaining a PM detection method according to the embodiment of the present invention.

FIG. 4 is a flowchart showing a content of PM detection control that is executed in the engine according to the embodiment of the present invention.

FIG. 5 is a flowchart showing a content of PM regeneration control which is executed in the engine according to the embodiment of the present invention.

FIG. 6 is a flowchart showing a content of PM detection request determination which is executed in the engine 10 according to the embodiment of the present invention.

FIG. 7 is one example of a map which sets the interval at which the PM detection control is executed in the engine 10 according to the embodiment of the present invention.

FIG. 8 is a flowchart showing contents of processings of determining establishment of the PM detection preconditions.

FIG. 9 is a flowchart showing contents of processings of determining establishment of the PM detection preconditions.

FIG. 10 is a flowchart showing contents of processings of determining establishment of the PM detection preconditions.

FIG. 11 is a flowchart showing a content of processing of determining establishment of a PM detection precondition.

FIG. 12 is a time chart showing examples of the operation action of the engine according to the embodiment of the present invention.

FIG. 13 is a time chart showing examples of the operation action of the engine according to the embodiment of the present invention.

FIG. 14 is a time chart showing examples of the operation action of the engine according to the embodiment of the present invention.

FIG. 15 is a diagram showing a modification of the engine according to the embodiment of the present invention.

DESCRIPTION OF EMBODIMENTS

FIG. 1 is a schematic diagram showing an internal combustion engine 10 according to an embodiment of the present invention. Hereinafter, the internal combustion engine 10 will be simply called as "the engine 10". In the present embodiment, the engine 10 is a gasoline engine. The engine 10 includes an engine main body 12 constructed of a cylinder block, a cylinder head, pistons, intake valves, exhaust valves and the like. The engine main body 12 has four cylinders which are aligned in series. The respective cylinders are provided with ignition plugs not illustrated. The engine 10 shown in FIG. 1 is of an in-line four-cylinder type, but in the present invention, the number of cylinders and cylinder disposition are not limited to this.

The engine 10 includes a fuel injection device 28. In each and every cylinder of the engine main body 12, port injection valves 29 that are connected to the fuel injection device 28 are disposed. An intake port of each of the cylinders of the engine main body 12 is connected to an intake manifold 14. In the intake manifold 14, an intake air temperature sensor (not illustrated) is disposed. From the intake manifold 14 toward an upstream side of an intake passage, a throttle 26, an intercooler 24 and an air flow meter 22 are sequentially provided. Fresh air is taken in from the air flow meter 22 side, and air is supplied to each of the cylinders of the engine main body 12 via the intake manifold 14. An opening degree of the throttle 26 is optionally controllable by an ECU 50 that will be described later.

An exhaust port of each of the cylinders of the engine main body 12 is connected to an exhaust manifold 16. A downstream side of the exhaust manifold 16 is connected to an exhaust passage 18. In the exhaust passage 18, an air-fuel ratio sensor (an A/F sensor) 52 is provided. A catalyst 36 is disposed downstream of the A/F sensor 52. The engine 10 includes a turbocharger 46. The turbocharger 46 includes a compressor provided downstream of the air flow meter 22 in the intake passage, and a turbine which is provided upstream of the A/F sensor 52 in the exhaust passage 18.

The engine 10 includes an EGR passage 39 to perform EGR (Exhaust Gas Recirculation) which recirculates part of an exhaust gas to the intake manifold 14. As shown in FIG. 1, one end of the EGR passage 39 is connected to the exhaust manifold 16, and the other end is connected to the intake manifold 14. Halfway through the EGR passage 39, an EGR cooler 40 and an EGR valve 42 are provided in sequence from the exhaust manifold 16 side. An opening degree of the EGR valve 42 is optionally controllable by the ECU 50 which will be described later.

The system of the present embodiment further includes the ECU (Electronic Control Unit) 50. A crank angle sensor (not illustrated) that detects a crank angle of the engine 10 is electrically connected to the ECU 50, in addition to the various sensors and actuators described above. An engine speed can be detected from an output from the crank angle sensor. The ECU 50 causes the respective actuators to operate in accordance with a predetermined program based on the outputs from the respective sensors, and thereby controls an operation state of the engine 10.

A heater 66 is provided inside the A/F sensor 52 as will be described later. Energization control of the heater 66 is performed by the ECU 50. The ECU 50 turns on the heater 66 at a time of start of the engine 10, and heats the A/F sensor 52 to a target temperature Ts which is set in advance to activate the A/F sensor 52. In the present embodiment, the target temperature Ts and a first temperature $T_1$ which will be described later have the same value. The first temperature $T_1$ is equal to or higher than an activation temperature of the A/F sensor 52. The ECU 50 performs control of an air-fuel ratio by using an output value from the A/F sensor 52 at the first temperature $T_1$. The ECU 50 controls the air-fuel ratio in a feedback manner by using the output value from the A/F sensor 52. When the engine 10 is a diesel engine, known feedback control is similarly applied to the engine 10. Air-fuel ratio control of the diesel engine is not a novel matter, and various kinds of feedback control in which EGR rates or fuel injection amounts are regulated based on the output values from the A/F sensors in diesel engines are already known. Therefore, explanation of the air-fuel ratio control of a diesel engine will be omitted.

As for energization control of the heater 66, feedforward control may be performed after a correlation of an energization amount of the heater 66 and a sensor element temperature is determined in advance, or the energization amount of the heater 66 may be feedback-controlled based on the sensor element temperature. Since it is a known art that element impedance has a correlation with the element temperature, the sensor element temperature may be estimated by detecting the element impedance, for example.

FIG. 2 is a view showing the A/F sensor 52 included by the engine 10 according to the embodiment of the present invention, and is a view showing a structure of a sensor element 60 of the A/F sensor 52. The sensor element 60 includes an insulating layer 61, a plate-shaped solid electrolyte 62 which is fixedly attached to the insulating layer 61, and a pair of electrodes (namely, an exhaust electrode 63 and an atmosphere electrode 64) which are installed on a front surface and a back surface of the solid electrolyte 62 so as to face each other. In the insulating layer 61, at a site facing the atmosphere electrode 64 at an inner side, an atmosphere chamber 65 is formed, so that the atmosphere electrode 64 is exposed to atmosphere. The heater 66 is buried in the insulating layer 61. A diffusion resistance layer 68 formed from porous ceramics, for example, is stacked on the exhaust electrode 63 and the solid electrolyte 62, and a shielding layer 69 is stacked on the diffusion resistance layer 68. An exhaust gas in an element atmosphere penetrates to an inside of the diffusion resistance layer 68 from inlet surfaces 68*a* of the diffusion resistance layer 68, and diffuses inside the diffusion resistance layer 68 to reach the exhaust electrode 63. At this time, a limiting current flows between the electrodes 63 and 64, and a sensor output value is generated based on the limiting current. The limiting current corresponds to an oxygen concentration of the gas which reaches the exhaust electrode 63.

In general, an A/F sensor is brought into an active state where the A/F sensor issues a practical sensor output at a stage where the A/F sensor reaches an activation temperature set in advance by being heated by a heater at a time of actuation. The A/F sensor 52 is active at the first temperature $T_1$ which is set in advance at a value lower than a PM combustion temperature. The A/F sensor 52 is kept in an active state in a temperature range equal to or higher than the first temperature $T_1$. As one example, the PM combustion temperature is approximately 500 degrees, and in this case, the first temperature $T_1$ may be set at a temperature between approximately 300 degrees and approximately 400 degrees, for example.

In order to obtain the A/F sensor 52 which is active at the first temperature $T_1$ which is lower than the PM combustion temperature, a material of the solid electrolyte 62 can be a material showing an oxygen ion conductivity which is necessary for air-fuel ratio measurement at a temperature lower than the PM combustion temperature. Solid electrolytes like this are already known, and for example, lanthanum silicate doped with magnesium, a lanthanum silicate material to which magnesium is not added, but composition change or the like is applied, perovskite NaBiTiO and the like are cited. The details of these materials are also described in Non Patent Literatures 1 to 3 which are mentioned above, and are not novel matters, and therefore, explanation thereof will be omitted. Further, the material of the solid electrolyte 62 is not limited to lanthanum silicate doped with magnesium and the like which are cited here, and other solid electrolytes showing high oxygen ion conductivities similarly to these materials at a temperature lower than the PM combustion temperature may be used.

In the conventional A/F sensor, zirconia is used in the solid electrolyte 62, and in zirconia, a sufficient oxygen ion conductivity cannot be obtained until the temperature becomes such a high temperature as about 600 degrees to 700 degrees. Therefore, the activation temperature of the conventional A/F sensor is a high temperature which is equal to or higher than 600 degrees. As compared with the conventional A/F sensor like this, the activation temperature of the A/F sensor 52 is lower.

The heater 66 can heat the A/F sensor 52 to a second temperature $T_2$ that is set in advance at a value equal to or higher than the PM combustion temperature. The second temperature $T_2$ is a temperature equal to or higher than the PM combustion temperature and is a temperature at which the A/F sensor 52 is in an active state, and may be set at approximately 600 degrees, for example. The sensor element 60 of the A/F sensor 52 is exposed to the exhaust passage 18, and therefore, PM in the exhaust gas accumulates on a surface of the diffusion resistance layer 68. When the A/F sensor 52 is heated to the second temperature $T_2$ by the heater 66, the accumulated PM can be combusted. The specific numeric values of the first temperature $T_1$ and the second temperature $T_2$ described above are only examples, and may be properly set in accordance with various conditions such as the PM combustion temperature and the material used in the solid electrolyte 62.

FIG. 3 is a diagram for explaining a PM detection method according to the embodiment of the present invention. Hereinafter, for convenience of explanation, an output value from the A/F sensor 52 at a time of the A/F sensor 52 being at the first temperature $T_1$ will be generically called "an output value $A_1$". Further, for convenience of explanation, an output value from the A/F sensor 52 at a time of the A/F sensor 52 being at the second temperature $T_2$ will be generically called "an output value $A_2$". In the PM detection method according to the present embodiment, PM is detected based on a difference ΔA between the output value $A_1$ and the output value $A_2$. The output value $A_2$ takes a plurality of different values in response to PM accumulation amounts, and in FIG. 3, output values $A_{20}$ to $A_{23}$ are illustrated. Further, the output value $A_1$ can also take different values in response to operation conditions of the engine 10. In an operation action example of the engine 10 shown in FIG. 12, the output value A1 takes different values $A_{11}$ and $A_{12}$ corresponding to the operation conditions, as examples.

FIG. 3 is a diagram illustrating sensor output characteristics 90, 92 and 94 and a reference sensor output characteristic 96 for explaining tendencies of the output values of the A/F sensor 52 in a case of the PM accumulation amounts differing. A vertical axis in FIG. 3 represents an output value A of the A/F sensor 52, and a horizontal axis represents a temperature T. FIG. 3 illustrates sensor output characteristics under preferable conditions in which the oxygen concentration in the exhaust gas is assumed to be fixed. The PM detection method mentioned here is preferably used under the operation conditions in which the oxygen concentration of the exhaust gas is fixed.

The sensor output characteristics 90, 92 and 94 schematically show sensor output-temperature characteristics at a time of heating the A/F sensor 52 to the second temperature $T_2$ from the first temperature $T_1$. The sensor output characteristic 90 is one example of the characteristic in a case where Pm is not accumulated on the A/F sensor 52, and is illustrated as showing a flat characteristic relatively to a temperature rise here. The sensor output characteristic 92 is one example of a characteristic in a case where a small amount of PM accumulates on the A/F sensor 52. The sensor output characteristic 94 is one example of a characteristic in a case where a large amount of PM accumulates on the A/F sensor 52. In the sensor output characteristics 92 and 94, reduction in the output values starts when the temperature reaches a temperature $T_{th}$. This schematically shows a state in which reduction in the oxygen concentration due to combustion of PM starts at the temperature $T_{th}$ or a higher temperature.

When PM accumulates on the A/F sensor 52, the oxygen concentration reduces with PM combustion when the A/F sensor 52 is heated to the second temperature $T_2$. The A/F sensor 52 issues an output that is substantially linear to the oxygen concentration, and therefore, as the oxygen concentration reduction amount following PM combustion is larger, the output value reduces proportionally. Referring to FIG. 3, with the sensor output characteristic 90 with the PM accumulation amount being zero, the output value $A_2$ is a value $A_{20}$, and the value $A_{20}$ is the same value as the output value $A_1$. With the sensor output characteristic 92, the PM accumulation amount is small, and the output value $A_2$ is a value $A_{21}$. In relation to this, with the sensor output characteristic 94 with the PM accumulation amount being large, the output value $A_2$ is a value $A_{22}$ which is a value smaller than the value $A_{21}$. Thereby, the difference ΔA between the output value $A_1$ and the output value $A_2$ has a correlation with the amount of PM which is accumulated in the A/F sensor 52.

The reference sensor output characteristic 96 is an output curve that is obtained when PM in "a reference PM amount" which is set in advance is accumulated. By comparing the reference sensor output characteristic 96 and the output value $A_2$ which is actually obtained from the A/F sensor 52, whether or not PM is accumulated can be detected. A predetermined value $A_0$ which is shown in FIG. 3 is a difference between an output value $A_{23}$ in the reference sensor output characteristic 96, and the output value $A_1$. The predetermined value $A_0$ is a value that is set in advance by an experiment or the like, and is stored in the ECU 50 in advance. When the difference ΔA calculated by the actual sensor outputs from the A/F sensor 52 is equal to or larger than the predetermined value $A_0$, it can be determined that PM in a larger amount than the "reference PM amount" is accumulated in the A/F sensor 52.

FIG. 3 illustrates a threshold value $A_{th}$. The threshold value $A_{th}$ can be obtained by subtracting the predetermined value $A_0$ from the output value $A_1$. The threshold value $A_{th}$ is a value set in advance, and is stored in the ECU 50 in advance. According to the threshold value $A_{th}$, it can be determined whether or not the PM accumulation amount reaches the reference PM amount. In other words, the threshold value $A_{th}$ is a value for determining an output deviation of the A/F sensor 52 at a time of setting the output value $A_1$ at the first temperature $T_1$ as a standard value. As described above, the difference ΔA between the output value $A_1$ and the output value $A_2$ has a correlation with the PM accumulation amount. The ECU 50 may be caused to perform determination processing of determining that the PM accumulation amount is smaller than the reference PM amount set in advance when the output value $A_2$ is larger than the threshold value $A_{th}$, and determining that the PM accumulation amount is equal to or larger than the reference PM amount when the output value $A_2$ is a value equal to or smaller than the threshold value $A_{th}$. The output values $A_{20}$ and $A_{21}$ illustrated in FIG. 3 are larger than the threshold value $A_{th}$, and therefore, it can be determined that the PM accumulation amount of this time is larger than the PM accumulation amount of the reference sensor output characteristic 96, that is, "the reference PM amount".

The threshold value $A_{th}$ may be made changeable in accordance with the operation conditions of the engine 10. The threshold value $A_{th}$ can be obtained by subtracting the predetermined value $A_0$ from the output value $A_1$. The output value $A_1$ takes different values in accordance with the operation conditions of the engine 10. FIG. 12 which will be described later shows one example of the operation action of the engine 10. In the operation action example illustrated in FIG. 12, the output value $A_1$ takes a certain value $A_{11}$ in a case of a fuel cut (F/C) and idle stop (also called stop and start: S & S and the like). Therefore, a first threshold value $A_{th1}$ may be set for fuel cut (F/C) and idle stop (S & S), by subtracting the predetermined value $A_0$ from the output value $A_{11}$. Further, in the operation action example in FIG. 12, the output value $A_1$ during an idle operation is a value $A_{12}$, and the output value $A_{12}$ is smaller than the output value $A_{11}$. Therefore, a second threshold value $A_{th2}$ that should be used during an idle operation may be set by subtracting the predetermined value $A_0$ from the output value $A_{12}$. Thereby, the threshold value $A_{th2}$ is set at a value smaller than the threshold value $A_{th1}$. However, the threshold values $A_{th1}$ and $A_{th2}$ mentioned here are only shown as specific examples, and the present invention is not limited to these threshold values. The actual threshold value $A_{th}$ can be set by investigating a correlation of the operation conditions and the output value $A_1$, by performing adaptation in an actual machine and the like.

The amount of PM may be calculated by using the fact that the difference ΔA between the output value $A_1$ and the output value $A_2$ has a correlation with the amount of PM which is accumulated in the A/F sensor 52. That is to say, a correlation between the difference ΔA and the PM accumulation amount is determined in advance by an experiment or the like, and a proportionality constant of these amounts may be fixed and stored in the ECU 50 in advance. Alternatively, a map in which a correspondence relation between the difference ΔA and the PM accumulation amount may be created, and may be stored in the ECU 50 in advance. The ECU 50 may execute calculation processing of calculating a larger amount of PM as the difference ΔA is larger, by using the proportionality constant or the map.

PM may be detected based on a ratio of the output value $A_1$ and the output value $A_2$ (that is, a value of "$A_2/A_1$") in place of the difference ΔA between the output value $A_1$ and the output value $A_2$. As the output value $A_1$ and the output value $A_2$ are closer to each other, the ratio of these values is closer to one. Accordingly, by comparing the value of the ratio of the output value $A_1$ and the output value $A_2$ with another threshold value which is set in advance, it can be also determined whether or not the PM accumulation amount is larger than the aforementioned "reference PM amount". Further, another proportionality constant may be set in advance by measuring a correlation between the ratio of the output value $A_1$ and the output value $A_2$, and the PM accumulation amount in advance. The ECU 50 may be caused to execute processing of calculating a larger PM accumulation amount as a value of "$A_2/A_1$" is smaller than 1, for example, by using the proportionality constant.

Since the A/F sensor 52 needs to be already in an active state at the first temperature $T_1$, the first temperature $T_1$ only has to be equal to or higher than the activation temperature of the A/F sensor 52, and the first temperature $T_1$ and the activation temperature of the A/F sensor 52 do not have to correspond to each other. In regard with this point, the value of the first temperature $T_1$ can be properly set from the following viewpoint, for example. For example, at a time of start of the engine 10, in order to bring the A/F sensor 52 into an active state quickly to use the sensor output thereof, the heater 66 is turned on, whereby the A/F sensor 52 is heated. Heating by the heater 66 is continued until the A/F sensor 52 reaches a target temperature Ts that is set in advance. The target temperature Ts is generally set at a temperature which is the same as the activation temperature at which the A/F sensor 52 starts to issue a practical output, or is higher than the activation temperature. The first temperature $T_1$ may be set at the same temperature as the target temperature Ts, or may be a temperature higher than the target temperature Ts. Further, an art of performing activation determination processing that determines whether or not the A/F sensor 52 becomes active at the time of start of the engine 10 or the like is already known. When a determination temperature to determine activation/inactivation is set in the known activation determination processing like this, the determination temperature for determining activation/inactivation and the first temperature $T_1$ do not necessarily have to correspond to each other. That is to say, the first temperature $T_1$ may be the same as the determination temperature, or the first temperature $T_1$ may be set to be higher than the determination temperature.

In the aforementioned embodiment, PM detection is performed by using the air-fuel ratio sensor 52, but the present invention is not limited to this. In place of the air-fuel ratio sensor 52, a known oxygen sensor that abruptly changes an output when the oxygen concentration exceeds a preset threshold value may be used. More specifically, by using a solid electrolyte composed of the material similar to the material of the solid electrolyte 62 in the known oxygen sensor, an oxygen sensor that issues an output corresponding to the oxygen concentration even at a temperature lower than the PM combustion temperature can be produced. In this oxygen sensor, the oxygen concentration also reduces with PM combustion when the oxygen sensor is heated to the second temperature $T_2$ when PM is accumulated, and therefore, an abrupt output change occurs when the oxygen concentration reduction amount exceeds the threshold value of the oxygen sensor. Conversely, when PM is not accumulated, or the PM accumulation amount is small, the PM combustion amount at the time of heating the oxygen sensor to the second temperature $T_2$ is zero or small. In this case, the oxygen concentration reduction amount with PM combustion is zero, or is too small to exceed the threshold value of the oxygen sensor, and therefore, an abrupt output change does not occur. Like this, as another embodiment of the present invention, PM can be also detected by using the oxygen sensor.

FIG. 4 is a flowchart showing a content of PM detection control that is executed in the engine 10 according to the embodiment of the present invention. In a routine shown in FIG. 4, the ECU 50 firstly determines whether or not a "PM detection request flag" is set (step S100). The "PM detection request flag" is a flag that is set according to a flowchart in FIG. 6 which will be described later, and is a flag indicating whether or not it is timing to execute the PM detection control. When the condition in step S100 is not established, it is not the timing to execute the PM detection control, and therefore, the routine of this time is ended.

When the PM detection request flag is set in step S100, the ECU 50 determines whether or not a "PM detection precondition flag" is set (step S102). The "PM detection precondition flag" is a flag which is set according to a flowchart in FIG. 8 which will be described later, and is a flag that indicates whether or not the precondition for the PM detection control is satisfied. When the condition in step S102 is not established, the precondition for the PM detection control is not satisfied, and therefore, the routine of the time is ended.

When the PM detection precondition flag is set in step S102, the ECU 50 determines whether or not the output value $A_1$ of the A/F sensor 52 is already acquired (step S104). When the output value $A_1$ is not acquired yet, the processing proceeds to S106, and the output value $A_1$ at the time of the A/F sensor 52 being at the first temperature $T_1$ is acquired. When the output value $A_1$ is already acquired, the processing skips step S106 and proceeds to step S108.

In step S108, the ECU 50 increases the energization amount of the heater 66. Thereby, the A/F sensor 52 is heated. Next, the ECU 50 is determined whether or not the present sensor element temperature is equal to or higher than the second temperature $T_2$ (step S110). When the condition in step S110 is not established, the sensor element temperature does not reach a temperature at which the output value $A_2$ should be acquired, and therefore, the routine of this time is ended, and the processing returns.

When the condition in step S110 is established, the sensor element temperature reaches the second temperature $T_2$ or a higher temperature at this time point, and therefore, the processing proceeds to step S112. In step S112, the output value $A_2$ is acquired. In the present embodiment, as one preferable mode, the ECU 50 acquires the output of the A/F sensor 52 at the time when a "first predetermined time period" which is set in advance elapses after the sensor element temperature reaches the second temperature $T_2$, as the output value $A_2$. By the processings of step S110 and S112, the output of the A/F sensor 52 at the time of the sensor element temperature reaching the second temperature $T_2$ can be acquired as the output value $A_2$.

Next, the ECU 50 calculates ΔA that is an absolute value of the difference between the output value $A_1$ and the output value $A_2$ (step S114). Subsequently, the ECU 50 calculates a PM amount PMm from the value of the ΔA by referring to a map or the like which is stored in advance (step S116). Next, the ECU 50 clears the PM detection request flag (step S118). Furthermore, the ECU 50 compares the difference ΔA with a predetermined value $A_0$ that is set in advance (step S120). When the difference ΔA is larger than the predetermined value $A_0$, the processing proceeds to step S122, and the ECU 50 sets a "PM regeneration request flag". The "PM regeneration request flag" is a flag to be a condition for executing "PM regeneration control" shown in a flowchart in FIG. 5 which will be described later. Note that "PM regeneration" refers to removing PM adhering to the A/F sensor 52 by oxidizing the PM. When the difference ΔA is equal to or smaller than the predetermined value $A_0$, the processing proceeds to step S124 to reduce the energization amount of the heater 66. Thereafter, the routine of this time is ended.

As described above, according to the present embodiment, the A/F sensor 52 is active at both the first and the second temperatures $T_1$ and $T_2$, and therefore, each of the plurality of sensor output values $A_1$ and $A_2$ for use in PM detection is a highly precise value. Accordingly, PM can be detected with high precision. Further, according to the present embodiment, the air-fuel ratio detection function and the PM detection function of the engine 10 can be made compatible with the one A/F sensor 52.

In step S112, the output value $A_2$ is obtained after a lapse of "the first predetermined time period", and concerning acquisition of the output value $A_2$, various modifications that will be described as follows are assumed. As schematically shown in FIG. 12 to FIG. 14 which will be described later, after heating to the second temperature $T_2$, the output value of the A/F sensor 52 temporarily drops from the first output value $A_1$ in conjunction with start of PM combustion. During combustion of PM, the output value of the A/F sensor 52 shows a value smaller than the first output value $A_1$. Thereafter, when heating by the heater 66 is stopped, the output value of the A/F sensor 52 increases, namely, restores to the first output value $A_1$ side.

By combusting PM by continuing to keep the sensor element temperature at the second temperature $T_2$, the PM accumulation amount is also reduced, and therefore, the output value of the A/F sensor 52 increases, namely, restores to the first output value $A_1$ side. When the sensor element temperature is continued to be kept at the second temperature $T_2$, the accumulated PM is decreased, and therefore, the output value of the A/F sensor 52 is close to a value at the time of the PM accumulation amount being zero. If the acquisition timing of the output value $A_2$ is too late, the output value of the A/F sensor 52 during PM combustion cannot be acquired as the output value $A_2$. Therefore, in order to avoid the acquisition timing of the output value $A_2$ from being too late, timing to acquire the output value $A_2$ is preferably made a time point when the aforementioned first predetermined time period elapses after a temperature rise to the second temperature $T_2$, of the sensor element temperature occurs. "The first predetermined time period" is a time period in which the timing to acquire the output value of the A/F sensor 52 is determined in order to acquire the output value of the A/F sensor 52 at the second temperature $T_2$ while PM is being combusted, namely, before PM is completely combusted. "The first predetermined time period" may be a fixed value that is set in advance, or may be a variable value that changes in accordance with a rule that is set in advance. As one preferable mode in a case of the first predetermined time being made a variable value, the ECU 50 may be caused to execute the following processing. First, the ECU 50 is caused to execute processing of calculating an estimated PM accumulation amount adhering to the A/F sensor 52 from the operation state of the engine 10. The ECU 50 stores, in advance, a mathematical expression, a map or the like which sets the first predetermined time period so that the first predetermined time period becomes a longer time period as the estimated PM accumulation amount is larger. The ECU 50 calculates the first predetermined time period corresponding to the estimated PM estimation amount of this time from the map or the like. More preferably, values of the above described map or the like are determined so as to make the first predetermined time period shorter than the time period in which PM is completely combusted, by determining the time period until PM in the estimated PM accumulation amount is completely combusted in advance by an experiment or the like.

Concerning step S112, to the processing of measuring the elapsed time period after the temperature rise of the sensor element temperature to the second temperature $T_2$ occurs, at least any one of the following processings (p1) to (p3) may be applied. The processings (p1) to (p3) are common in the viewpoint of measuring the elapsed time period in response to the temperature rise of the sensor element temperature to the second temperature $T_2$, but differ from one another in a starting point of the elapsed time period.

(p1) As one example of a starting point of the time measurement, the ECU 50 may start time measurement with the time point when the sensor element temperature coincides with the second temperature $T_2$. The sensor element temperature may be estimated based on the element impedance of the A/F sensor 52 as described above. Like this, the time period after the sensor element temperature reaches the second temperature $T_2$ may be compared with the first predetermined time period.

(p2) As another example of a starting point of the time measurement, the ECU 50 may start time measurement with a time point of an output rise start of the heater 66. In this case, the ECU 50 may compare a value obtained by subtracting a "temperature rise delay time period" from the measured time period, with the first predetermined time period. The "temperature rise delay time period" is a time period until the sensor element temperature reaches the second temperature $T_2$ after rise of the output of the heater 66. Thereby, an elapsed time period after the start of the temperature rise of the sensor element temperature to the second temperature $T_2$ may be compared with the first predetermined time period. That is to say, the starting point of time measurement discussed in this embodiment does not necessarily made the time point when the sensor element temperature coincides with the second temperature $T_2$.

(p3) As yet another example of a starting point of the time measurement, the ECU 50 may start time measurement with a time point when the sensor element temperature coincides with the PM combustion temperature stored in advance. Thereby, an elapsed time after PM starts combustion may be compared with the first predetermined time period.

Even in a time period in which the sensor element temperature is kept at the second temperature $T_2$, the output value of the A/F sensor 52 is not constant when it is seen on a time axis. Therefore, as one preferable mode, a peak value at a lower limit side of the curve which is drawn by the output value of the A/F sensor 52 while the sensor element temperature is kept at the second temperature $T_2$ may be set at the output value $A_2$. As another preferable mode, a plurality of output values of the A/F sensor 52 may be sampled while the sensor element temperature is kept at the second temperature $T_2$. Among the plurality of output values of the A/F sensor 52, which are sampled, a smallest value may be set at the output value $A_2$. The smallest value among the sampled values does not necessarily have to be a lower limit peak value in analog value of the output from the A/F sensor 52. The map or the like for calculating the PM amount PMm in step S116, and the predetermined value $A_0$ or the like used in step S120 may be created by being adapted to the above described various modifications with respect to step S112.

As is schematically shown in FIG. 12 to FIG. 14, as a longer time period elapses after heating to the second temperature $T_2$, the output of the A/F sensor 52 is more clearly reduced. Accordingly, setting of the above described first predetermined time period enhances output precision of the PM accumulation amount, and is therefore, preferable. However, the present invention is not limited to this, and the first predetermined time period does not have to be provided. At the time point when the sensor element temperature reaches the second temperature $T_2$, PM starts combustion, and therefore, an influence of PM combustion appears on the output value of the A/F sensor 52. Therefore, the output value of the A/F sensor 52 is acquired at the same time as the sensor element temperature reaches the second temperature $T_2$, and the value may be set as the output value $A_2$.

In step S120, it may be determined whether or not the output value $A_2$ is below a threshold value $A_{th}$. Further, as already described, PM can be detected based on the ratio of the output value $A_1$ and the output value $A_2$. Accordingly, the processing in step S120 in the routine in FIG. 4 can be replaced with processing of determining whether or not the ratio of the output value $A_1$ and the output value $A_2$ is within a range which is set in advance.

After the A/F sensor 52 is heated to the second temperature $T_2$ from the first temperature $T_1$ with the heater 66, two output values before and after the heating are preferably used as the output value $A_1$ and the output value $A_2$. However, the present invention is not limited to this, and two output values which are separated in terms of time may be used. For example, although heating control by the heater 66 is started after acquisition of the output value $A_1$, heating of the heater 66 can be stopped before the sensor element temperature reaches the second temperature $T_2$ for some reason. If heating of the heater 66 is restarted thereafter, the A/F sensor 52 is heated, and the output value $A_2$ can be obtained. In such a case, the difference $\Delta A$ between the output value $A_2$ and the output value $A_1$ which are separated in terms of time is calculated, and may be used in PM detection.

In the aforementioned embodiment, a temperature rise from the first temperature $T_1$ to the second temperature $T_2$ is realized by heating of the heater 66, but the present invention is not limited to this. The output value $A_2$ at the second temperature $T_2$ may be acquired without depending on heating of the heater 66. As a specific example, when the engine 10 is operated under the operation conditions in which the exhaust temperature is a high temperature, the sensor element temperature can reach a temperature equal to or higher than the PM combustion temperature without increasing the output of the heater 66. The operation condition in which the sensor element temperature reaches the temperature equal to or higher than the PM combustion temperature like this may be set and stored in the ECU 50 in advance as "a high exhaust temperature operation condition". At a time of establishment of the high exhaust temperature operation condition, the output value of the A/F sensor 52 is acquired, and the sensor output value may be used as the output value $A_2$. In this case, one of the heater 66 and the high exhaust temperature operation condition may correspond to "heating means" to heat the A/F sensor 52 to the second temperature $T_2$.

In the aforementioned embodiment, control is performed in sequence of acquiring the output value $A_2$ after acquiring the output value $A_1$. However, the present invention is not limited to this, and after one of the output value $A_1$ and the output value $A_2$ is acquired, the other one can be acquired. That is to say, sequence may be opposite from the sequence in the embodiment. More specifically, the output value $A_2$ is acquired when the A/F sensor 52 is at the second temperature $T_2$, and thereafter, the output value $A_1$ may be acquired in the stage at which the temperature of the A/F sensor 52 drops to the first temperature $T_1$. Irrespective of sequence of acquiring the output value $A_1$ and the output value $A_2$, the relation between the output value of the A/F sensor 52 and the sensor element temperature shown in FIG. 3 is established, and therefore, the PM accumulation amount can be detected.

FIG. 5 is a flowchart showing a content of PM regeneration control which is executed in the engine 10 according to the embodiment of the present invention. The "PM regeneration control" controls the heater 66 so as to keep the A/F sensor 52 at the PM combustion temperature or a higher temperature. More specifically, in a routine in FIG. 5, the ECU 50 firstly determines whether or not the PM regeneration request flag is set (step S200). The PM regeneration request flag is a flag which is set in step S122 in FIG. 4 described above.

When the PM regeneration request flag is not set, it is not timing to execute the PM regeneration control, and therefore, the routine of this time is ended. When the PM regeneration request flag is set, the ECU 50 subsequently determines whether or not the sensor element temperature is lower than a "PM regeneration temperature" which is set in advance (step S204). The "PM regeneration temperature" is a target temperature at which the sensor element temperature should be kept in the PM regeneration control, and is a value which is determined in advance. The PM regeneration temperature is a temperature which is set in advance to be equal to or higher than the PM combustion temperature (approximately 500° C. as an example). In the present embodiment, explanation is performed on the assumption that the PM regeneration temperature and the second temperature $T_2$ are the same temperature, but the present invention is not limited to this, and the PM regeneration temperature may be set at a temperature lower than the second temperature $T_2$ or a temperature higher than the second temperature $T_2$. When the condition in step S204 is not established, the ECU 50 increases the energization amount of the heater 66 (step S206), and thereafter, proceeds to step S208. When the condition in step S204 is established, the ECU 50 proceeds to step S208 while keeping the energization amount of the heater 66.

In step S208, the ECU 50 determines whether or not at least one of two conditions X1 and X2 as follows is established.

(Condition X1) The output value of the A/F sensor 52 is equal to or larger than a predetermined value which is set in advance. The predetermined value is set in advance as a value for determining whether or not PM is sufficiently combusted and removed from the A/F sensor 52 and the output value is restored.

(Condition X2) A regeneration time period is equal to or longer than a second predetermined time period which is set in advance. The "regeneration time period" is a length of a time period in which the sensor element temperature is kept to be equal to or higher than the PM regeneration temperature, as an example. The regeneration time period may be measured by performing time measurement by a timer included by the ECU 50 from a time point at which the sensor element temperature reaches the PM regeneration temperature, for example.

When both the condition X1 and the condition X2 are not established, the determination result in step S208 is determined as negative (NO). In this case, the routine of this time is ended, and the processing returns, whereby the processing in step S200 and the following processings are repeated again. As a result, the A/F sensor 52 is kept at the PM regeneration temperature until either the condition X1 or X2 is established. When at least one of the condition X1 and the condition X2 is established, the determination result in step S208 is determined as affirmative (YES).

When the determination result in step S208 is affirmative, the ECU 50 reduces the energization amount of the heater 66 (step S210). The ECU 50 reduces the energization amount of the heater 66 to a usual energization amount which keeps the sensor element temperature at the first temperature $T_1$. Thereafter, the PM regeneration request flag is cleared (step S212), and the routine of this time is ended.

FIG. 6 is a flowchart showing a content of PM detection request determination which is executed in the engine 10 according to the embodiment of the present invention. The "PM detection request determination" determines whether or not a request to execute PM detection control described with FIG. 4 is present. In a routine in FIG. 6, the ECU 50 firstly determines whether or not a predetermined time period TPMI which is set in advance elapses from PM detection control of the previous time (step S300). More specifically, the ECU 50 includes processing of storing a time point at which the PM detection control is ended, and stores the latest PM detection control end time point. In step S300, it is determined whether or not an elapsed time period from the end time point to the present time point is equal to or longer than the predetermined time period TPMI which is set in advance. When the elapsed time period is shorter than the predetermined time period TPMI, the routine of this time is ended.

When it is determined that the elapsed time period is equal to or longer than the predetermined time period TPMI in step S300, the processing proceeds to step S302. In step S302, the ECU 50 determines whether or not the A/F sensor 52 is in an active state. More specifically, it is determined whether or not the A/F sensor 52 reaches the activation temperature. When the A/F sensor 52 is not in an active state, the routine of this time is ended. When the A/F sensor 52 is in an active state, the processing proceeds to step S304, and the PM detection request flag is set.

When the PM detection control is performed, the A/F sensor 52 is heated to the second temperature $T_2$, and therefore, the PM accumulation amount in the A/F sensor 52 decreases. If the PM detection control is repeated in a short time period, the A/F sensor 52 is heated to the second temperature $T_2$ even though PM is not accumulated so much. This is not preferable because useless electric power is consumed by the heater 66. According to the processing in step S300, PM detection control of the next time is not performed until the predetermined time period TPMI which is set in advance elapses after the PM detection control of the previous time. Therefore, the interval of the PM detection control is restrained from becoming too small, and useless power consumption by the heater 66 can be restrained.

FIG. 7 is one example of a map which sets the interval at which the PM detection control is executed in the engine 10 according to the embodiment of the present invention. In the map in FIG. 7, a relation between the output value $A_2$ and the aforementioned predetermined time period TPMI is set. The predetermined time period TPMI is a minimum interval at which the PM detection control should be executed. As described with FIG. 3, as the PM accumulation amount is smaller, the output value $A_2$ indicates a higher value, and the difference $\Delta A$ becomes smaller. If the PM accumulation amount is small, the interval at which the PM detection control is executed may be long. Therefore, in the map in FIG. 7, the relation between both the output value $A_2$ and the predetermined time period TPMI is set so that as the output value $A_2$ is larger, the predetermined time period TPMI becomes longer. The ECU 50 preferably perform "time setting control" that sets the predetermined time period TPMI to be longer as the PM detection amount which is acquired at the previous time is smaller, in accordance with the map shown in FIG. 7.

FIG. 8 to FIG. 10 are flowcharts showing contents of processings of determining establishment of the PM detection preconditions, which are executed in the engine 10 according to the embodiment of the present invention. Routines in FIG. 8 to FIG. 10 are preferably executed when the engine 10 is mounted on a vehicle. According to the routines in FIG. 8 to FIG. 10, it can be determined whether or not preferable implementation conditions of the PM detection control are satisfied.

In the routine shown in FIG. 8, the PM detection precondition is set by a relation with fuel cut. In the routine in FIG. 8, the ECU 50 firstly determines whether a fuel cut (F/C) flag is set (step S400). When it is determined that the F/C flag is set in step S400, the ECU 50 determines whether or not the output of the A/F sensor 52 is equal to or larger than a prescribed value set in advance (step S402). The prescribed value is set to be the same value as the output value indicated by the A/F sensor 52 in atmosphere corresponding to air. When the condition in step S402 is established, fresh air is introduced into the cylinders, as a result that fuel cut is executed, and an environment in which an exhaust gas oxygen concentration is substantially fixed is created. In the environment like this, the PM detection control can be performed with high precision. Therefore, the processing proceeds to step S404, the ECU 50 sets the PM detection precondition flag, and the routine of this time is ended.

When the condition in step S400 or step S402 is negated, the processing proceeds to step S406, and the ECU 50 clears the PM detection precondition flag. Thereafter, the ECU 50 determines whether or not the sensor element temperature is equal to or higher than a lower limit value which is set in advance. When the sensor element temperature is below the lower limit value, the routine of this time is ended, and the processing returns. When the sensor element temperature is equal to or higher than the lower limit value, the ECU 50 reduces the energization amount of the heater 66 (step S410). Thereafter, the routine of this time is ended.

In the routine shown in FIG. 9, the PM detection precondition is set by a relation with idle stop (S&S). Except for steps S500 and S502, the contents in FIG. 9 and FIG. 8 are the same. In the routine in FIG. 9, it is determined whether or not the engine 10 is stopping by idle stop (S&S) first in step S500. When it is determined that the engine 10 is not under idle stop (S&S) in step S500, the processing of S406 and the following processings are executed as in FIG. 8. When it is determined that the engine 10 is under idle stop (S&S) in step S500, the ECU 50 subsequently determines whether or not the engine speed of the engine 10 is below a detection upper limit value Neth which is set in advance (step S502). When the engine speed is equal to or higher than Neth in step S502, the processing proceeds to step S406. When the engine speed is below Neth in step S502, the PM detection precondition flag is set, and the routine of this time is ended.

In the routine shown in FIG. 10, the PM detection precondition is set by a relation with an idle operation. Except for steps S600 and S602, the contents in FIG. 10 and FIG. 8 are the same. In the routine in FIG. 10, it is firstly determined whether or not the engine 10 is idling in step S600. When it is determined that the engine 10 is not idling in step S600, the processing in step S406 and the following processings are executed as in FIG. 8. When it is determined that the engine 10 is idling in step S500, the ECU 50 subsequently determines whether or not the output value of the A/F sensor 52 indicates a value within a fixed range which is set in advance to be close to a theoretical air-fuel ratio (step S602). When the output value of the A/F sensor 52 deviates from the above described fixed range in step S602, the processing proceeds to step S406. When the condition in step S602 is established, the PM detection precondition flag is set, and the routine of this time is ended.

According to the routines in FIG. 8 to FIG. 10 described above, the PM detection control can be executed in at least one time period of the time periods during fuel cut, during an idle operation and during idle stop. In these time periods, the exhaust gas oxygen concentration is substantially fixed, and PM can be detected with high precision.

FIG. 11 is a flowchart showing a content of processing of determining establishment of a PM detection precondition, which is executed in the engine 10 according to the embodiment of the present invention. In the routine in FIG. 11, the ECU 50 firstly executes processing of determining whether or not the operation condition of the engine 10 corresponds to a predetermined condition that is set in advance in which the A/F sensor 52 is likely to be covered with water, in step S700. The predetermined condition is a condition which corresponds to a time of cold start of the engine 10, for example. When it is determined that the operation condition of the engine 10 corresponds to the predetermined condition, the routine of this time is ended. When it is determined that the operation condition of the engine 10 does not correspond to the predetermined condition in step S700, the flow shifts to step S404, and the PM detection precondition flag is set. Thereafter, the routine of this time is ended.

If the high-temperature A/F sensor 52 is covered with water, there arises the problem of breakage occurring to the sensor element 60. When the PM detection control is performed, the A/F sensor 52 is heated to the second temperature $T_2$, and therefore, it is not preferable to perform the PM detection control when there is a high probability of the A/F sensor being covered with water. In this regard, according to the routine in FIG. 11, when there is a high probability of the A/F sensor 52 being covered with water, the PM detection precondition flag is not set. Thereby, breakage of the sensor element can be restrained.

FIG. 12 to FIG. 14 are time charts showing examples of the operation action of the engine 10 according to the embodiment of the present invention. FIG. 12 is a time chart at a time of carrying out fuel cut. FIG. 13 is a time chart at a time of carrying out idle stop (S&S). FIG. 14 is a time chart at a time of carrying out idle.

The time charts in FIG. 12 to FIG. 14 are on the precondition that the A/F sensor 52 is in an active state. That is to say, when the engine 10 starts, the heater 66 is turned on, and in order to bring the A/F sensor 52 into an active state, the A/F sensor 52 is heated to the target temperature Ts. In the operation action examples mentioned here, the first temperature $T_1$ is set at the same value as the target temperature Ts. Thereafter, the A/F sensor 52 reaches the first temperature $T_1$, and the A/F sensor 52 becomes active. The A/F sensor 52 becomes active, whereby the ECU 50 starts control using the output value of the A/F sensor 52, more specifically, A/F feedback control. Thereafter, the engine 10 is operated as usual.

First of all, an operation action at the time of fuel cut will be described with use of FIG. 12. At a time point $t_0$ in FIG. 12, fuel cut is started in the engine 10. As a result of the fuel cut is started, an intake air amount is reduced, and the output value of the A/F sensor 52 increases to a prescribed value which is set at an atmosphere level. Though not illustrated, at this point of time, the "PM detection precondition flag" is set according to the routine in FIG. 8. Thereafter, at a time point $t_1$, the PM detection request flag is set. In response to this, the conditions in steps S100 and S102 in the routine in FIG. 4 are both established. As a result, the first output value $A_1$ is stored in step S104, and the heater energization amount is increased in step S108. Thereafter, the sensor element temperature reaches the second temperature $T_2$, and the condition in step S110 in the routine in FIG. 4 is established. After the first predetermined time period which is set in advance and is described in step S112 elapses from the time point $t_1$, a time point $t_2$ arrives. Thereafter, in accordance with the processing in step S112 and the following processings, the ECU 50 acquires the output value $A_2$, calculates the difference $\Delta A$, calculates the PM amount PMm, and clears the PM detection request flag. In the operation action example shown in FIG. 12, the output value of the A/F sensor 52 with a large PM accumulation amount is below the threshold $A_{th}$, as in the solid line in the FIG. 12. In this case, in step S122 in FIG. 4, the PM regeneration request flag is set, and further, the ECU 50 executes the PM regeneration control shown in FIG. 5. In the operation action example in FIG. 12, the regeneration time period is regarded as reaching a second predetermined time period which is set in advance at a time point $t_3$, and the heater energization amount is reduced. Therefore, after the time point $t_3$, PM combustion is stopped, and the output value of the A/F sensor 52 increases, and is restored to the value before the time point $t_1$. Thereafter, at a time point $t_4$, fuel cut is ended, and acceleration starts. In FIG. 12, the output value of the A/F sensor 52 in the case of the PM accumulation amount being large is illustrated by a solid line, and in addition, the output value of the A/F sensor 52 in the case of the PM accumulation amount being small is illustrated by a broken line for comparison. In "PM ACCUMULATION AMOUNT [g]" at the lowest stage in FIG. 12, a graph in a case of the PM accumulation amount being large is illustrated by the solid line, and a graph in a case of the PM accumulation amount being small is illustrated by the broken line, respectively. This also applies to FIG. 13 and FIG. 14 as follows. When a change in the PM accumulation amount in a time period from the time point $t_1$ to the time point $t_2$ is seen, a combustion speed is higher as the PM accumulation amount is larger.

Next, an operation action at the time of idle stop (S&S) will be described with use of FIG. 13. At a time point $t_{10}$ in FIG. 13, idle stop (S&S) is started in the engine 10. At the time point $t_{10}$ when idle stop (S&S) is started, the intake air amount, the vehicle speed and the engine speed become zero. Though not illustrated, at a time point when the engine speed becomes lower than a detection upper limit value Neth, the "PM detection precondition flag" is set according to the routine in FIG. 9. In FIG. 13, as an example, the output value of the A/F sensor 52 increases to an atmosphere level after the time point $t_{10}$, and thereafter, the output value of the A/F sensor 52 gradually reduces to stoichiometry. In FIG. 13, as one example, at timing when the output value of the A/F sensor 52 reaches stoichiometry, the PM detection request flag is set. In response to the PM detection request flag being set at a time point $t_{11}$, the conditions in steps S100 and S102 in the routine in FIG. 4 are both established. As a result, the first output value $A_1$ is stored in step S104, and the heater energization amount is increased in step S108. After the first predetermined time period which is set in advance and is described in step S112 elapses from the time point $t_{11}$, a time point $t_{12}$ arrives. Thereafter, the ECU 50 executes acquisition of the output value $A_2$ and the following respective processings as described with respect to the time points $t_3$ to $t_4$ in FIG. 12. Thereafter, at a time point $t_{13}$, idle stoop (S&S) is ended, and acceleration is started.

Next, an operation action at the idle time will be described with use of FIG. 14. At a time point $t_{20}$ in FIG. 14, fuel cut is started in the engine 10. Thereafter, at a time point $t_{21}$, fuel cut is ended. Fuel injection is restarted in response to the end of fuel cut, the air-fuel ratio is temporarily made rich, and the output value of the A/F sensor 52 shows that the air-fuel ratio is rich. At a time point $t_{22}$, the rich operation is ended. Though not illustrated, when the output value of the A/F sensor 52 indicates a theoretical air-fuel ratio after the rich operation is ended, the "PM detection precondition flag" is set according to the routine in FIG. 10. Thereafter, the PM detection request flag is set at a time point $t_{23}$, and the condition in step S100 in the routine in FIG. 4 is established. At the time point $t_{23}$ and thereafter, the PM detection request flag is set as described with respect to the time points $t_1$ to $t_3$ in FIG. 12, and the ECU 50 increases the heater energization amount, acquires the output value A2, and executes the following respective processings. Thereafter, the ECU 50 starts acceleration at a time point $t_{26}$.

FIG. 15 is a diagram showing a modification of the engine 10 according to the embodiment of the present invention. In the modification shown in FIG. 15, two A/F sensors 52 and 54 are disposed upstream and downstream of the catalyst 36. There is known an art of determining activation of the catalyst 36 by using the two A/F sensors 52 and 54 like them. When PM detection control or PM regeneration control are carried out, the A/F sensors 52 and 54 reach the second temperature $T_2$ at which the A/F sensors 52 and 54 are heated. Thereby, accumulated PM is combusted, and therefore, output deviations occur to the A/F sensors 52 and 54 due to PM combustion. Accordingly, when the processing of determining catalyst activation is executed, the A/F sensors 52 and 54 are preferably kept to be lower than the PM combustion temperature. Therefore, in the modification, as a routine that determines the precondition of the PM detection control, processing of determining whether or not catalyst activation determination processing is under execution is further added. When it is determined that the catalyst activation determination processing is under execution, the PM detection request flag is not set. Thereby, the catalyst activation determination processing and the PM detection control can be restrained from being executed at the same time.

REFERENCE SIGNS LIST 10 internal combustion engine
12 engine main body
14 intake manifold
16 exhaust manifold
18 exhaust passage
22 air flow meter
24 intercooler
26 throttle
28 fuel injection device
29 port injection valves
36 catalyst
39 EGR passage
40 EGR cooler
42 EGR valve
46 turbocharger
52 A/F sensor
60 sensor element
61 insulating layer
62 solid electrolyte
63 exhaust electrode
64 atmosphere electrode
65 atmosphere chamber
66 heater
68 diffusion resistance layer
68a inlet surface
69 shielding layer

The invention claimed is:

1. An internal combustion engine, comprising:
an oxygen concentration sensor that is provided in an exhaust passage, the oxygen concentration sensor including a solid electrolyte, wherein the oxygen concentration sensor is configured to be activated at a first temperature which is lower than a PM combustion temperature and is set in advance, and a second temperature which is equal to or higher than the PM combustion temperature and is set in advance; and
an electronic control unit programmed to execute PM detection control that detects PM based on an output value of the oxygen concentration sensor,
wherein the PM detection control comprises
(i) acquiring one output value of a first output value of the oxygen concentration sensor at a time of the oxygen concentration sensor being at the first temperature, and a second output value of the oxygen concentration sensor at a time of the oxygen concentration sensor being at the second temperature,
(ii) acquiring an other output value of the first output value and the second output value after acquiring the one output value,
(iii) detecting PM based on a difference between or a ratio of the first output value and the second output value,
wherein the second output value is acquired at a same time as the oxygen concentration sensor reaches the second temperature, or at a time when a predetermined time period which is set in advance elapses after a temperature rise of the oxygen concentration sensor to the second temperature occurs.

2. The internal combustion engine according to claim 1, further comprising:
a heater to heat the oxygen concentration sensor to the second temperature,
wherein the PM detection control further comprises
heating the oxygen concentration sensor to the second temperature with the heater after acquiring the first output value, and
after heating to the second temperature by the heater, acquiring an output value of the oxygen concentration sensor at a time when the predetermined time period elapses, as the second output value.

3. The internal combustion engine according to claim 2, wherein the electronic control unit is programmed to execute PM regeneration control,
wherein the PM regeneration control comprises controlling the heater to keep the oxygen concentration sensor at the PM combustion temperature or a higher temperature than the PM combustion temperature when a difference between or a ratio of an output value of the oxygen concentration sensor at the first temperature and an output value of the oxygen concentration sensor at the second temperature is larger than a value set in advance, after heating the oxygen concentration sensor to the second temperature with the heater.

4. The internal combustion engine according to claim 1, wherein the electronic control unit is programmed
not to perform the PM detection control of a next time until a predetermined time period which is set in advance elapses, after executing the PM detection control, and
to execute time setting control that sets the predetermined time period to be longer as a reduction amount of the second output value relative to the first output value in the PM detection control of a previous time is smaller.

5. The internal combustion engine according to claim 1, wherein the electronic control unit is programmed to execute the PM detection control in at least one of time periods during fuel cut, during an idle operation and during idle stop.

6. The internal combustion engine according to claim 1, wherein the electronic control unit is programmed not to execute the PM detection control when an operation condition of the internal combustion engine corresponds to a condition set in advance under which the oxygen concentration sensor is likely to be covered with water.

7. The internal combustion engine according to claim 1, wherein the PM detection control further comprises calculating a larger amount of PM, as a detected reduction amount is larger, the detected reduction amount being a reduction amount of an output value of the oxygen concentration sensor at a time of the second temperature relative to the output value of the oxygen concentration sensor at a time of the first temperature.

* * * * *